United States Patent [19]

Rumberger

[11] Patent Number: 5,118,410

[45] Date of Patent: Jun. 2, 1992

[54] DEBRIS COLLECTING AND MEASURING DEVICE WITH INDUCTION COIL SCREEN

[75] Inventor: William E. Rumberger, Newton Square, Pa.

[73] Assignee: The Boeing Company, Seattle, Wash.

[21] Appl. No.: 544,941

[22] Filed: Jun. 28, 1990

[51] Int. Cl.⁵ ............................................. G01N 15/06
[52] U.S. Cl. .................................... 210/85; 73/64; 73/64.61; 210/243; 324/204; 340/631
[58] Field of Search ...................... 73/64; 210/85, 243; 324/204; 340/631; 55/270

[56] References Cited

U.S. PATENT DOCUMENTS

| | | | |
|---|---|---|---|
| 2,349,992 | 5/1944 | Schrader | 340/631 |
| 3,373,352 | 3/1968 | Huigens | 324/204 |
| 3,502,970 | 3/1970 | Thayer | 73/64 |
| 3,686,926 | 8/1972 | Miller et al. | 73/61 R |
| 3,748,576 | 7/1973 | Sigournay | 340/631 |
| 3,753,442 | 8/1973 | Tauber | 137/15 |
| 3,878,103 | 4/1975 | Miller et al. | 210/243 |
| 4,066,962 | 1/1978 | Jaffe | 324/208 |
| 4,070,660 | 1/1978 | Tauber | 340/236 |
| 4,091,958 | 5/1978 | Zemke | 220/291 |
| 4,199,443 | 4/1980 | Tauber | 210/85 |
| 4,219,805 | 8/1980 | Magee et al. | 340/631 |
| 4,279,748 | 7/1981 | Inoue | 210/222 |
| 4,282,016 | 8/1981 | Tauber et al. | 55/204 |
| 4,286,404 | 9/1981 | Tauber et al. | 73/293 |
| 4,302,754 | 11/1981 | Magee et al. | 340/631 |
| 4,657,671 | 4/1987 | Botstiber et al. | 210/86 |
| 4,755,288 | 7/1988 | Mitchell | 210/85 |
| 4,878,019 | 10/1989 | Tsaprazis et al. | 324/204 |
| 5,001,424 | 3/1991 | Kellett et al. | 340/631 |
| 5,027,065 | 6/1991 | Bares et al. | 324/204 |
| 5,028,318 | 7/1991 | Aslin | 210/85 |
| 5,061,364 | 10/1991 | Metala et al. | 210/85 |

Primary Examiner—W. Gary Jones
Assistant Examiner—Joseph Drodge
Attorney, Agent, or Firm—Jones, Tullar & Cooper

[57] ABSTRACT

An inductive coil shaped screen traps debris in a fluid and senses the accumulation of the debris. The shaped screen coil comprises non-conductive wires parallel to one another and at least one conductive wire coil perpendicular and woven with the non-conductive wires. The conductive wire is a coil of an inductor. As debris accumulates within the coil, inductance immediately changes and indicates the accumulation of debris in the screen. Another coil connects with the first coil in a bridge circuit to compensate for changes in temperature of the fluid.

5 Claims, 2 Drawing Sheets

DEBRIS COLLECTING AND MEASURING DEVICE WITH INDUCTION COIL SCREEN

The present invention relates to an electrical apparatus for sensing debris in a fluid. More specifically, the present invention relates to an electrical inductive apparatus for indicating the accumulation of debris in a fluid.

BACKGROUND OF THE INVENTION

Fluid systems serving, for example, a lubricating function in mechanical power transmitting systems become contaminated by wear particles from the various components of the mechanical system. For example, bearings and gears are known to spall and to produce so-called "debris" which enters the fluid system.

It is known to utilize this phenomenon of wear particles as a means of detecting the integrity of the mechanical system. Detection is achieved by monitoring the fluid system.

One such apparatus is described in U.S. Pat. No. 3,878,103 and a related apparatus is disclosed in U.S. Pat. No. 3,686,926. Both patents describe an apparatus for detecting debris in the fluid of hydraulic, lubricating, or cooling systems, for instance. These apparatuses comprise a sensor housing and a woven mesh screen within the housing. The fluid of the system enters the sensor housing and flows through the screen. The screen comprises a pair of electrical conductors of opposite polarity and a non-conductive wire woven with the electrical conductors. The debris, such as metal spall flakes or chips from a transmission bathed in the fluid of the system, contacts the pair of conductors and completes an electrical circuit. The apparatus is responsive to electrical conductivity that occurs between the pair of conductors and through the spall flake or chip, and produces a signal indicating the presence of the spall flake or chip. The apparatus includes a pressure sensor that indicates the accumulation of debris on the screen.

Though the pressure sensor indicates accumulation of debris, the pressure sensor of the noted patents does not indicate sufficiently small uniform increments of the accumulation of debris. Since the presence of small amounts of debris in the fluid is not always detectable, the time period in which a threshold amount of debris accumulates before that amount can be detected by the pressure sensor, is not always sufficient. Furthermore, the limited number of electrical circuits available in the screen would prevent an accurate measurement of debris accumulation using this conductivity technique.

SUMMARY OF THE INVENTION

There continues to be a need for a full flow debris monitoring apparatus which can monitor any amount of accumulation of failure debris generation within a fluid system. According to the present invention an indicating screen provides a means of capturing and indicating the presence of debris particles and of constantly monitoring debris accumulation in uniform increments.

The apparatus of the present invention comprises a screen sensor having a coil shaped screen that holds the debris. The coil shaped screen comprises linear, non-conductive segments parallel to one another and at least one conductive wire perpendicular and woven with the linear, non-conductive segments. The conductive wire produces an inductance which can be used to monitor, or indicate the accumulation of debris in the coil shaped screen, coil.

As debris accumulates within, the screen/coil, the inductance of the coil shaped screen correspondingly changes, which provides an indication of the accumulation of debris in the coil shaped screen. In addition, it is possible to determine the rate of accumulation of debris in the coil shaped screen.

A second inductor is connected with the coil shaped screen as a first inductor in a bridge circuit to thereby effect compensation for changes in temperature of the fluid.

BRIEF DESCRIPTION OF THE FIGURES

Four figures have been selected to describe a preferred embodiment of the invention. While these figures are schematic, they are sufficient for those skilled in the art to practice the invention. Included are.

DETAILED DESCRIPTION OF THE INVENTION

Figure 1:
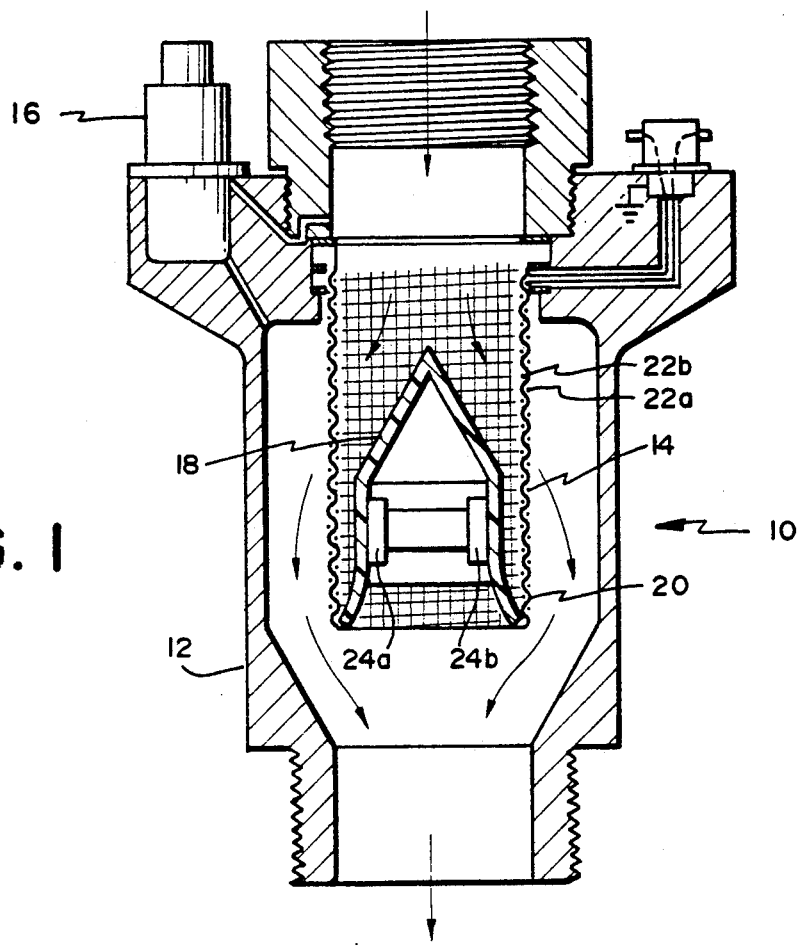
FIG. 1, which shows an inductive screen sensor of the invention.

FIG. 1 shows an inductive screen sensor 10 according to the present invention. The screen sensor 10 comprises a metal housing 12, open at both ends to allow fluid, such as hydraulic, lubricating, or cooling fluid, to flow through in the direction indicated by the arrows. A cylindrical inductive coil shaped screen 14 is mounted in the flow path of the fluid that passes through the screen sensor 10. The inductive coil shaped screen 14 traps any debris flowing with the fluid, and, according to the present invention, is responsive to the accumulation of debris.

Preferably, the mesh of the coil shaped screen 14 is sized to trap debris larger than 0.005 inches. The debris trapped by the coil shaped screen 14 is typical of failure debris and must be monitored closely, because this debris indicates the possibility of a complete failure of a system aboard an aircraft, for example. Smaller debris passes with the fluid through the coil shaped screen 14. The debris passed by the coil shaped screen 14 is typical of wear debris and is considered normal. The coil shaped screen 14 is preferably woven in one of the Leno weaves described in the noted patents, for example. The portions of the specifications of the noted patents that describe the Leno weaves are incorporated by reference.

The screen sensor 10 includes a pressure differential switch 16 and a conical portion 18, as described in the noted patents. The portions of the specifications of the noted patents describing the pressure differential switch and conical portion are also incorporated by reference.

Figure 2:
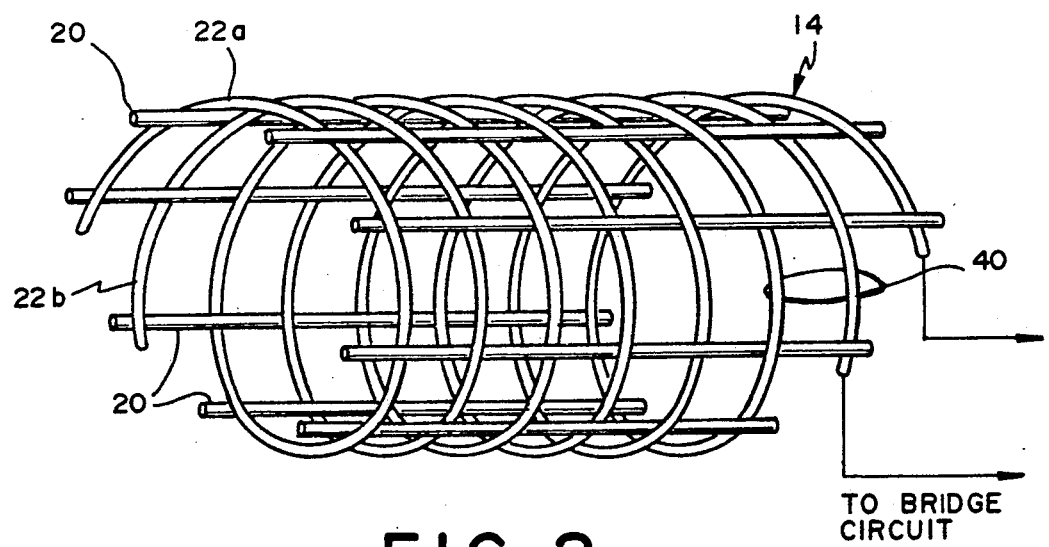
FIG. 2, which shows an inductive coil shaped screen of the screen sensor of FIG. 1.

FIG. 2 shows the inductive coil shaped screen 14 of the screen sensor 10 of FIG. 1. The coil shaped screen 14 comprises linear segments 20 of non-conductive wires, for example. The linear segments 20 can comprise a number of separate, parallel non-conductive wires, or one continuous non-conductive wire folded upon itself in S-curves. In the case of one continuous wire, straight portions of the wire comprise the linear segments that parallel one another.

The inductive coil shaped screen 14 also comprises at least one conductive wire 22a. The conductive wire is woven between and is substantially perpendicular to the linear segments 20 of the non-conductive wires. In this case, the conductive wire 22a forms coils of an inductor having a desired number of turns. When an alternating current signal is applied to the conductive wire 22a, the conductive wire 22a produces a flux field density and, thus, has an inductance value. This inductance value remains relatively constant in the absence of debris and serves as a reference value. However, in the presence of debris, the inductance value of the conductive wire 22a changes. Such debris is typically a ferrous material comprising metal spall flakes or chips from a mechanism, such as a transmission, which a fluid carries to the inductive coil shaped screen 14. For example, a trapped chip 40 lies adjacent the conductive wire 22a. The presence of the chip 40 adjacent the conductive wire 22a interferes with the flux field density generated around the conductive wire 22a and accordingly changes the inductance of the coil shaped screen 14. This change in inductance vs. time indicates a change in the accumulation of debris within the screen sensor 10 in an incremental manner. From this information a rate of accumulation of debris can also be detected.

Tests have been conducted concerning the principle of the present invention. An inductive screen as described above was connected to a 4192A LF Impedance Analyzer (5 Hz to 13 MHz) manufactured by Hewlett-Packard Co. For simplicity, a bolt, representing debris that might be trapped in the inductive coil shaped screen 14, was placed inside the inductive coil shaped screen and various frequency AC signals were sequentially applied to the conductive wire of the inductive coil shaped screen. The table below illustrates that changes in inductance indicate the presence of the bolt within the inductive coil shaped screen over a range of frequencies.

| FREQUENCY (@ 1 volt) | INDUCTANCE (in micro-henries) | |
| --- | --- | --- |
| | Without Bolt | With Bolt |
| 100 Hz | 20 | 30 |
| 400 Hz | 10 | 20 |
| 1 KHz | 6 | 10 |
| 5 KHz | 6 | 8 |
| 10 KHz | 5.3 | 6.7 |
| 100 KHz | 5.18 | 5.33 |
| 1 MHz | 4.961 | 5.170 |

The selected frequency determines such phenomenon as skin effect which can be used to prioritize the sensing of debris.

The inductive screen/coil can comprise the single coiled conductive wire 22a or a number of parallel coils, such as 22a and 22b of any number of turns. Furthermore, a number of coils can be wound in the mesh of the screen/coil, one next to another along the length of the screen/coil, which is horizontal as viewed in FIG. 2. In any case, each conductive wire is coated with insulation and is similar to the high temperature magnet wire commonly used in winding coils of transformers. The conductive wire 22a of the inductive screen/coil 14, is electrically connected to a bridge circuit, such as the bridge circuit of FIG. 3.

Figure 3:
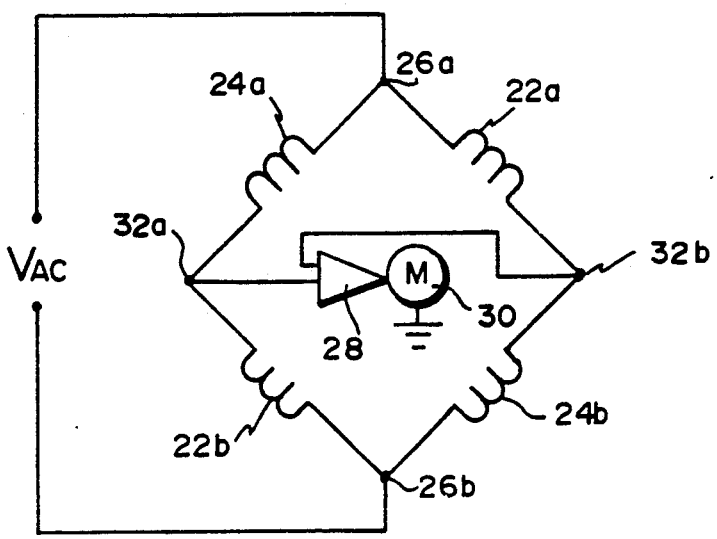
FIG. 3, which shows a schematic diagram of a bridge-circuit with temperature compensation for the screen sensor of FIG. 1.

FIG. 3 shows a schematic diagram of a bridge circuit with temperature compensating for the screen sensor of FIG. 1. Though the inductance of the conductive wire 22a is relatively constant in the absence of debris, the inductance can change due to changes in temperature of the fluid passing through the screen sensor 10. For example, when monitoring a transmission, the inductance would change when the temperature of the transmission oil changes from cold start-up temperatures to normal hot operating temperatures.

In the temperature compensating circuit of FIG. 3, two conductive wires 22a and 22b are connected as two legs of the bridge circuit in this example. Two other conductive wires 24a and 24b (FIG. 4) comprise temperature compensating wires that connect to the conductive wires 22a and 22b in the bridge circuit. In FIG. 1, the compensating wires 24a, 24b are shown as sensors mounted to the conical portion 18 and connected to the bridge circuit.

In place of the conductive wires 24a and 24b, resistances could be employed.

Figure 4:
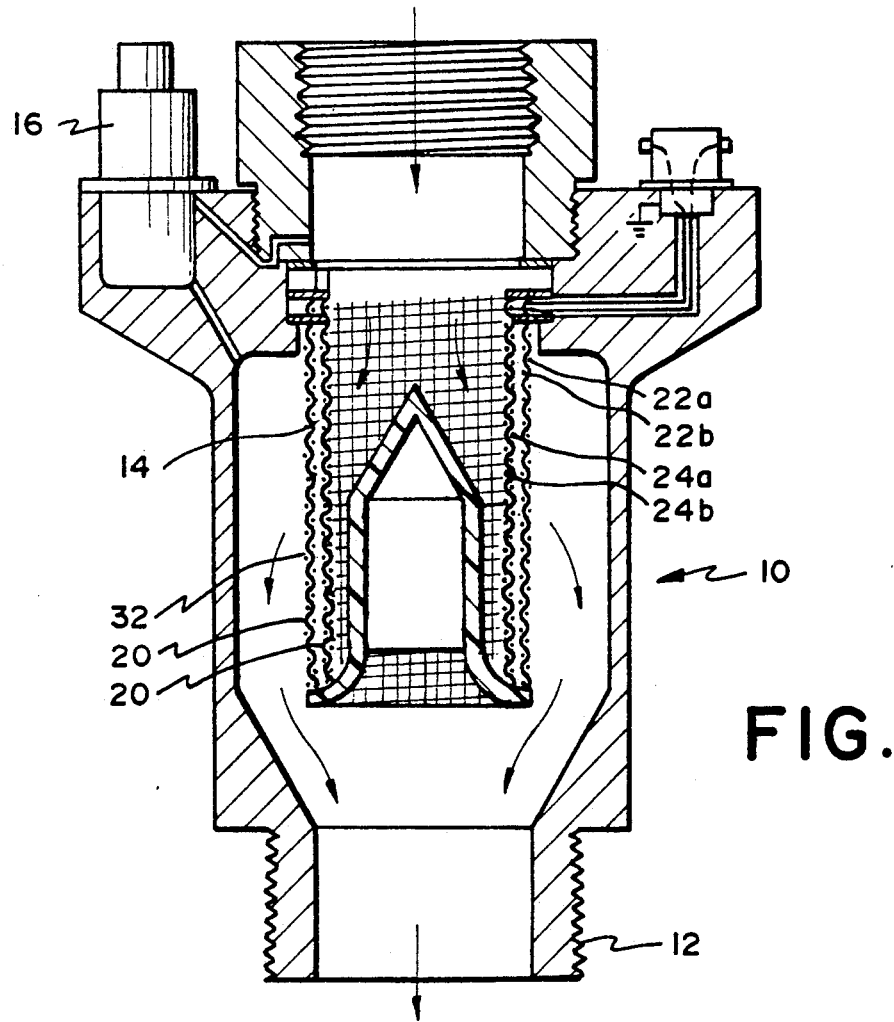
FIG. 4, which shows an inductive screen sensor having a compensating coil.

A voltage Vac is applied across the bridge circuit at a junction 26a of the conductive wires 22a and 24a and the junction 26b of the conductive wires 22b and 24b. An amplifier 28 and a meter 30 are connected to the bridge circuit across junctions 32a and 32b. The meter indicates changes in inductance of the conductive wires 22a and 22b. Inductance values are correlated to an amount of debris in a The bridge circuit of FIG. 3 uses the coiled conductive wires 24a and 24b as inductive, temperature compensating elements in the circuit. As the temperature of the fluid changes in the sensor 10, inductances of each of the wires 22a, 22b, 24a, and 24b also change. However, the coiled conductive wires are arranged in the bridge circuit of FIG. 3 to compensate for such temperature changes. The coiled wires are also arranged to indicate changes in inductance of the wires 22a and 22b that are caused by other than temperature changes of the fluid. Specifically, the coiled conductive wires are arranged to indicate changes in inductance of the conductive wires 22a and 22b caused by the presence of debris in the inductive coil-shaped screen 14. With this invention, there is no delay in indicating such a change, compared to the response of pressure sensitive systems that require the accumulation of a threshold amount of debris before a change is indicated. The debris does not, however, change the inductance of the wires 24a and 24b, because these wires are positioned outside the inductive coil shaped screen 14, as shown in FIG. 4. Thus, inductance of only the conductive wires 22a and 22b changes in response to debris and inductance of all the wires 22a, 22b, 24a, and 24b changes according to the temperature of the fluid passing through the sensor.

FIG. 4 shows an inductive screen sensor having an inductive coil shaped screen 14 and a parallel outer screen 32 that surrounds the inductive screen/coil 14. The outer screen 32 constitutes the temperature compensating element that comprises the coiled conductive wires 24a of FIG. 3, for example. The coiled wires 24a is part of the outer screen 32 that parallels the inductive screen 14. A second conductive wire that comprises the inductor 24b of FIG. 3 is also part of the outer screen 32. The location of the temperature compensating coil elements, wire 24a and 24b, can be varied to obtain additional sensing benefits from mutual coupling effects of separate flux fields. The arrangement of FIG. 4 obtains such benefits.

What is claimed is:

1. An apparatus for sensing debris in a fluid and indicating the accumulation of debris, comprising:
   coil-shaped screen means for holding debris of at least a given size and establishing an accumulation of the debris, said coil-shaped screen means including a coil-shaped screen having linear, non-conductive segments parallel to one another and at least one conductive wire woven with the linear non-conductive segments and directed substantially perpendicular to said linear, non-conductive segments, an inductor; and
   means for measuring an inductive change due to the accumulation of the debris on said coil-shaped screen, such that said at least are conductive wire functions as an induction coil, indicating thereby, the accumulation of the debris in said coil-shaped screen.

2. An apparatus for sensing debris in a fluid and indicating the accumulation of debris, comprising:
   coil-shaped screen means for holding debris of at least a given size and establishing an accumulation of the debris, said coil-shaped screen means including a coil-shaped screen having linear, non-conductive segments parallel to one another and at least one conductive wire woven with the linear non-conductive segments and directed substantially perpendicular to said linear, non-conductive segments,; and means comprising
   a bridge circuit with said at least one conductive wire forming a leg of the bridge circuit, for measuring an inductive change due to the accumulation of the debris on said coil-shaped screen, such that said at least are conductive wire functions as an induction coil, indicating thereby, the accumulation of the debris in said coil-shaped screen.

3. The apparatus as defined in claim 2, wherein said coil shaped screen has a further conductive wire woven with the linear, non-conductive segments to compensate for temperature change in the fluid, with said further conductive wire forming another leg of the bridge circuit.

4. The apparatus as defined in claim 3 wherein each of said at least one conductive wires has a coating of insulation thereon.

5. The apparatus as defined in claim 2, wherein a further screen is provided situated parallel to said coil shaped screen to compensate for temperature change in the fluid, with said further screen forming another leg of the bridge circuit.

* * * * *

UNITED STATES PATENT AND TRADEMARK OFFICE
CERTIFICATE OF CORRECTION

PATENT NO. : 5,118,410

DATED : June 2, 1992

INVENTOR(S) : William E. Rumberger

It is certified that error appears in the above-identified patent and that said Letters Patent is hereby corrected as shown below:

Claim 1, column 5, line 10, a "," (second occurrence) should be deleted;
                        line 11, "an inductor" should be deleted; and
                        line 14, "are" should be "one".

Claim 2, column 6, line 3, a "," should be "deleted"; and
                        line 8, "are" should be "one".

Claim 3, column 6, line 12, a "-" should be inserted between "coil" and "shaped".

Claim 5, column 6, line 21, a "-" should be inserted after "coil".

Signed and Sealed this

Seventeenth Day of August, 1993

*Attest:*

BRUCE LEHMAN

*Attesting Officer*      Commissioner of Patents and Trademarks